United States Patent [19]

Howe

[11] 4,166,732

[45] Sep. 4, 1979

[54] OXADIAZOL-5-YL-BENZOATES

[75] Inventor: Robert K. Howe, Bridgeton, Mo.

[73] Assignee: Monsanto Company, St. Louis, Mo.

[21] Appl. No.: 796,255

[22] Filed: May 12, 1977

[51] Int. Cl.$^2$ .................... A01N 9/22; A01N 5/00
[52] U.S. Cl. ............................................. 71/92; 71/76
[58] Field of Search ...................................... 71/92, 76

[56] References Cited

U.S. PATENT DOCUMENTS

| 3,947,263 | 3/1976 | Brouwer et al. | 71/76 |
| 3,964,896 | 6/1976 | Brouwer et al. | 71/92 |

*Primary Examiner*—Catherine L. Mills
*Attorney, Agent, or Firm*—Richard H. Shear; Donald W. Peterson

[57] ABSTRACT

This invention relates to the use of oxadiazol-5-yl-benzoates as agricultural chemicals.

1 Claim, No Drawings

OXADIAZOL-5-YL-BENZOATES

This invention relates to the use of oxadiazol-5-yl-benzoates as agricultural chemicals. These compounds have been found to be effective in controlling the growth of undesired vegetation. At lower rates, the compounds have been found to be effective in regulating the growth of desirable plants.

The compounds of the invention may be represented by the following chemical formula

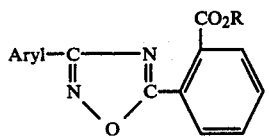

wherein R is selected from the group consisting of hydrogen, lower alkyl and agriculturally acceptable cations.

The term "Aryl" as used herein is understood to include pyridyl.

In accordance with known procedures, the oxadiazol-5-yl-benzoates may be prepared by reaction of the appropriate benzamide oxime with phthalic anhydride. The benzamide oxime may be prepared by reaction of a benzonitrile with hydroxylamine. The following examples are presented as illustrations of the above process.

EXAMPLE 1

Preparation of 2-[3-[3,5-Bis(Trifluoromethyl)Phenyl]-1,2,4-Oxadiazol-5-yl]Benzoic Acid A mixture of 26.35 g (0.0968 mol) of 3,5-bis(trifluoromethyl)benzamide oxime and 14.34 g (0.0968 mol) of phthalic anhydride in 475 ml of xylene was heated at reflux with stirring under a Dean-Stark water trap for 4.5 hours. The solvent was distilled off, and the residue was heated at 195°–200° C. for a few minutes, allowed to cool to 120° C., and dissolved in 400 ml of ethanol. The ethanol solution was allowed to stand for two days, and the resultant 7.53 g of solid, mp 102°–111° C., was filtered off.

The ethanol filtrate was concentrated to 150 ml and was diluted to 500 ml with water to give 1.9 g of solid, mp 102°–231° C., which infrared analysis showed to be a mixture of oxadiazole and phthalimide. The aqueous ethanol filtrate was diluted further with water to give 13 g of solid, mp 130°–170° C. This solid was crystallized twice from benzene to give 6.85 g of solid, mp 178.5°–182° C., which was recrystallized from 150 ml of water - 225 ml of ethanol to give 5.68 g of white solid, 2-[3-[3,5-bis(trifluoromethyl)phenyl]-1,2,4-oxadiazol-5-yl]benzoic acid, mp 182°–184° C.

Anal. Calc'd. for $C_{17}H_8F_6N_2O_3$: C, 50.76; H, 2.00. Found: C, 50.79; H, 2.01.

EXAMPLE 2

Preparation of 2-[3-(3,4-Dichlorophenyl)-1,2,4-Oxadiazol-5-yl]Benzoic Acid

A mixture of 14.17 g (0.0691 mol) of 3,4-dichlorobenzamide oxime and 10.24 g (0.0691 mol) of phthalic anhydride was heated gently with stirring to about 90° C., at which time a very vigorous exotherm carried the temperature to above 170° C.; the mixture was cooled in water to 130° C. and held at 130° C. for a few minutes, and then was cooled to 25° C. The mixture was extracted with 1 liter of ethanol and was filtered to give 3.5 g of insoluble solid, mp 200°–215° C.

The ethanol extract was diluted with 1.5 liters of water to give 6.1 g of solid, mp 185°–195° C., which was crystallized twice from $CH_3CN$ and once from benzene (filtration) to give 3.85 g of white solid, mp 202°–204° C.

Anal. Calc'd. for $C_{15}H_8Cl_2N_2O_3$: C, 53.76; H, 2.41. Found: C, 53.70; H, 2.42.

EXAMPLE 3

Preparation of Ethyl 2-[3-[3,5-Bis(Trifluoromethyl)Phenyl]-1,2,4-Oxadiazol-5-yl]Benzoate A solution of 2.1 g of 2-[3-[3,5-bis(trifluoromethyl)phenyl]-1,2,4-oxadiazol-5-yl]benzoate in 10 ml of thionyl chloride was held at reflux on a steam bath for 45 minutes, was concentrated under vacuum, and was diluted to 20 ml with ethanol. The ethanol solution was heated at reflux for 30 minutes, filtered, and concentrated under vacuum to 90° C. at 0.3 torr to give 2.15 g of very viscous oil.

Anal. Calc'd. for $C_{19}H_{12}F_6N_2O_3$: C, 53.03; H, 2.81. Found: C, 53.17; H, 2.83.

Salts may be prepared by reacting the free acid with the appropriate base. The following examples are illustrative thereof.

EXAMPLE 4

Preparation of 2-[3-[3,5-Bis(Trifluoromethyl)Phenyl]-1,2,4-Oxadiazol-5-yl]Benzoic Acid, Triethanolamine Salt Warm solutions of 2.0 g (0.00497 mol) of acid in 50 ml of ethyl acetate and 0.74 g (0.00497 mol) of triethanolamine in 30 ml of ethyl acetate were mixed and allowed to stand a few hours. The resultant solid, 2.44 g, mp 142°–143.5° C., was collected.

Anal. Calc'd. for $C_{23}H_{23}F_6N_3O_6$: C, 50.10; H, 4.20. Found: C, 50.08; H, 4.32.

EXAMPLE 5

Preparation of 2-[3-(3,4-Dichlorophenyl)-1,2,4-Oxadiazol-5-yl]Benzoic Acid, Triethanolamine Salt A solution of 2.0 g (0.00598 mol) of acid in 120 ml of warm ethyl acetate was added to a solution of 0.89 g (0.00598 mol) of triethanolamine in 30 ml of warm ethyl acetate. After a few hours, the resultant white solid, 2.60 g, mp 120°–122° C., was collected.

Anal. Calc'd. for $C_{21}H_{23}Cl_2N_3O_6$: C, 52.08; H, 4.79. Found: C, 52.11; H, 4.83.

In accordance with the above procedures, the following compounds have been prepared.

| Example | Compound |
|---|---|
| 6 | Ethyl 2-[3-(3-Trifluoromethylphenyl)-1,2,4-Oxadiazol-5-yl]Benzoate; $n_D^{25}$ 1.5385. Anal. Calc'd. for $C_{18}H_{13}F_3N_2O_3$: C, 59.67; H, 3.62 Found: C, 59.61; H, 3.62. |
| 7 | Ethyl 2-[3-Phenyl-1,2,4-Oxadiazol-5-yl]Benzoate; $n_D^{25}$ 1.5823. |
| 8 | Ethyl 2-[3-(1-Naphthyl)-1,2,4-Oxadiazol-5-yl]-Benzoate; $n_D^{25}$ 1.6282. Anal. Calc'd. for $C_{21}H_{16}N_2O_3$: C, 73.24; H, 4.68. Found: C, 73.35; H, 4.68. |

| Example | Compound |
|---------|----------|
| 9 | Ethyl 2-[3-(4-Chlorophenyl)-1,2,4-Oxadiazol-5-yl]Benzoate, mp 76.5°–77.5° C. Anal. Calc'd. for $C_{17}H_{13}ClN_2O_3$: C, 62.11; H, 3.99. Found: C, 62.05; H, 4.00. |

Preferred are those oxadiazol-5-yl-benzoates in which the Aryl is phenyl or phenyl substituted by one or more halogen, trifluoromethyl, lower alkyl or lower alkoxy moieties.

As used herein, the term "lower alkyl" or "lower alkoxy" is understood to mean those alkyl or alkoxy groups having from 1 to 5 carbon atoms, inclusive.

The term "agriculturally acceptable cations" is understood to mean those cations which are commonly used in herbicidal compositions to form the salt of the free acid, including but not limited to the alkali metal, substituted amine and ammonium cations.

As noted above, the compounds of the present invention have been found to be effective in the partial or total inhibition of undesirable vegetation. Tables I and II summarize results of tests conducted to determine the pre-emergent as well as the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 4 weeks after seeding and treating, the plants were observed and the results recorded. Tables I and II, below, summarize such results. The herbicidal rating was obtained by means of a fixed scale based on the percent injury of each plant species. The ratings are defined as follows:

| % Control | Rating |
|-----------|--------|
| 0–24 | 0 |
| 25–49 | 1 |
| 50–74 | 2 |
| 75–100 | 3 |

The post-emergent tests were conducted as follows:

The active ingredients are applied in spray form to two or three week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects ranging from no response to total inhibition are observed and recorded. The results are shown in Tables I and II in which the post-emergent herbicidal activity index is as follows:

| % Control | Rating |
|-----------|--------|
| 0–24 | 0 |
| 25–49 | 1 |
| 50–74 | 2 |
| 75–99 | 3 |
| 100 | 4 |

The plant species utilized in these tests are identified by letter in accordance with the following legend:

| | |
|---|---|
| A Soybean | I Hemp Sesbania |
| B Sugarbeet | J Lambsquarters |
| C Wheat | K Smartweed |
| D Rice | L Velvet Leaf |
| E Sorghum | M Bromus Tectorum |
| F Cocklebur | N Panicum Spp. |
| G Wild Buckwheat | O Barnyard Grass |
| H Morning Glory | P Crabgrass |

TABLE I

| Compound | WAT* | kg/h | Pre-Emergent Plant Species | | | | | | | | | | | | | | | |
|---|---|---|---|---|---|---|---|---|---|---|---|---|---|---|---|---|---|
| | | | A | B | C | D | E | F | G | H | I | J | K | L | M | N | O | P |
| 2 | 4 | 1.12 | 0 | 1 | 0 | 2 | 0 | 0 | 1 | 1 | 2 | 1 | 2 | 1 | 2 | 0 | 1 | 0 |
| | 4 | 5.60 | 1 | 2 | 2 | 2 | 1 | 0 | 1 | 2 | 2 | 1 | 1 | 1 | 2 | 0 | 2 | 1 |
| 3 | 2 | 1.12 | 0 | 0 | 0 | 1 | 0 | 0 | 0 | 0 | 0 | 0 | 0 | 0 | 0 | 0 | 1 | 0 |
| | 4 | 5.60 | 1 | 1 | 1 | 1 | 2 | 1 | 1 | 1 | 0 | 0 | 2 | 1 | 1 | 0 | 1 | 2 |
| 6 | 4 | 1.12 | 1 | 3 | 0 | 3 | 1 | 1 | 3 | 1 | 3 | 3 | 2 | 1 | 0 | 3 | 3 | 0 |
| | 4 | 5.60 | 3 | 2 | 2 | 3 | 2 | 2 | 1 | 2 | 2 | 3 | 2 | 1 | 1 | 0 | 3 | 3 |
| 8 | 2 | 1.12 | 0 | 1 | 3 | 2 | 0 | 1 | 0 | 1 | 1 | 0 | 0 | 3 | 0 | 0 | 3 | 0 |
| | 4 | 1.12 | 0 | 1 | 3 | 1 | 0 | 1 | 0 | 2 | 1 | 1 | 1 | 3 | 0 | 0 | 3 | 0 |
| | 2 | 5.60 | 0 | 1 | 0 | 3 | 0 | 1 | 1 | 1 | 1 | 0 | 1 | 0 | 1 | 0 | 2 | 0 |
| | 4 | 5.60 | 0 | 1 | 0 | 3 | 0 | 1 | 3 | 1 | 2 | 2 | 3 | 1 | 0 | 0 | 3 | 1 |
| 9 | 2 | 1.12 | 0 | 1 | 0 | 1 | 0 | 0 | 0 | 0 | 1 | 0 | 1 | 0 | 1 | 0 | 0 | 0 |
| | 4 | 5.60 | 0 | 2 | 1 | 2 | 1 | 2 | 0 | 2 | 2 | 3 | 3 | 1 | 0 | 0 | 3 | 2 |

*Weeks after treatment

| Compound | WAT* | kg/h | Post-Emergent Plant Species | | | | | | | | | | | | | | | |
|---|---|---|---|---|---|---|---|---|---|---|---|---|---|---|---|---|---|
| | | | A | B | C | D | E | F | G | H | I | J | K | L | M | N | O | P |
| 1 | 2 | 1.12 | 1 | 0 | 0 | 0 | 1 | 1 | 1 | 0 | 0 | 0 | 3 | 0 | 0 | 0 | 0 | 0 |
| | 4 | 5.60 | 1 | 1 | 0 | 0 | 1 | 1 | 1 | 1 | 1 | 1 | 4 | 0 | 0 | 0 | 0 | 0 |
| 5 | 4 | 1.12 | 1 | 1 | 1 | 0 | 1 | 1 | 0 | 1 | 1 | 1 | 2 | 1 | 0 | 0 | 0 | 0 |
| | 4 | 5.60 | 2 | 2 | 1 | 1 | 2 | 2 | 2 | 2 | 2 | 2 | 4 | 1 | 0 | 1 | 1 | 0 |
| 6 | 4 | 1.12 | 2 | 2 | 1 | 1 | 1 | 1 | 0 | 2 | 2 | 2 | 1 | 1 | 0 | 0 | 2 | 1 |

TABLE I-continued

| | | | | | | | | | | | | | | | | |
|---|---|---|---|---|---|---|---|---|---|---|---|---|---|---|---|---|
| 4 | 5.60 | 2 | 2 | 2 | 1 | 2 | 2 | 1 | 2 | 2 | 2 | 2 | 2 | 1 | 1 | 2 | 2 |

*Weeks after treatment

The compounds were further tested by utilizing the above procedure on the following plant species:

| | | |
|---|---|---|
| A Canada Thistle | E Lambsquarters | I Johnson Grass |
| B Cocklebur | F Smartweed | J Downy Brome |
| C Velvet Leaf | G Nutsedge | K Barnyard Grass |
| D Morning Glory | H Quackgrass | |

The results are summarized by Table II.

Table II

| Compound | WAT* | kg/h | \multicolumn{11}{c}{Pre-Emergent Plant Species} |
|---|---|---|---|---|---|---|---|---|---|---|---|---|---|

| Compound | WAT* | kg/h | A | B | C | D | E | F | G | H | I | J | K |
|---|---|---|---|---|---|---|---|---|---|---|---|---|---|
| 1 | 4 | 11.2 | 3 | 1 | 1 | 1 | 3 | 2 | 0 | 1 | 1 | 1 | 1 |
| 2 | 4 | 11.2 | 1 | 0 | 1 | 2 | 2 | 2 | 0 | 3 | 1 | 0 | 2 |
| 3 | 4 | 11.2 | 3 | 0 | 0 | 1 | 1 | 1 | 0 | 2 | 0 | 2 | 2 |
| 4 | 2 | 11.2 | 1 | 1 | 0 | 1 | 1 | 0 | 0 | 1 | 1 | 1 | 1 |
| 5 | 4 | 11.2 | 1 | 0 | 1 | 1 | 1 | 1 | 0 | 2 | 0 | 0 | 1 |
| 6 | 4 | 11.2 | 3 | 1 | 2 | 3 | 3 | 3 | 2 | 3 | 2 | 3 | 3 |
| 7 | 4 | 11.2 | 2 | 0 | 2 | 2 | 1 | 0 | 2 | 0 | 0 | 1 | 2 |
| 8 | 4 | 11.2 | 3 | 2 | 1 | 2 | 1 | 0 | 0 | 1 | 0 | 0 | 3 |
| 9 | 4 | 11.2 | 1 | 0 | 2 | 2 | 2 | 3 | 0 | 1 | 0 | 1 | 3 |

*Weeks after treatment

| Compound | WAT* | kg/h | A | B | C | D | E | F | G | H | I | J | K |
|---|---|---|---|---|---|---|---|---|---|---|---|---|---|
| | | | \multicolumn{11}{c}{Post-Emergent Plant Species} | | | | | | | | | | |
| 1 | 4 | 11.2 | — | 1 | 0 | 4 | 4 | 4 | 0 | 2 | 1 | 0 | 2 |
| 2 | 4 | 11.2 | 1 | 1 | 1 | 1 | 1 | 2 | 0 | 0 | 0 | 0 | 1 |
| 3 | 4 | 11.2 | 1 | 1 | 1 | 1 | 1 | 2 | 0 | 1 | 1 | 0 | 1 |
| 4 | 4 | 11.2 | 1 | 1 | 0 | 1 | 1 | 2 | 0 | 0 | 0 | 0 | 1 |
| 5 | 4 | 11.2 | 2 | 1 | 1 | 1 | 2 | 3 | 1 | 1 | 1 | 0 | 1 |
| 6 | 4 | 11.2 | 2 | 2 | 2 | 2 | 3 | 4 | 2 | 2 | 2 | 2 | 2 |
| 7 | 4 | 11.2 | — | 1 | 1 | 1 | 2 | 0 | 0 | 0 | 0 | 0 | 0 |
| 8 | 4 | 11.2 | 0 | 2 | 1 | 2 | 1 | 1 | 0 | 0 | 0 | 0 | 1 |
| 9 | 2 | 11.2 | 0 | 0 | 0 | 1 | 0 | 0 | 0 | 0 | 0 | 0 | 0 |

*Weeks after treatment

The above tables illustrate one aspect of the present invention. That is, the use of the compounds of the invention to kill or injure undesirable plants, e.g. weeds. Another aspect of the invention, however, is the use of said compounds, with the exception of Compound 4, for the regulation of desirable plant growth especially dicotyledonous plants such as legumes and trees.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth, it does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transistory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

Utilizing the oxadiazol-5-yl-benzoates of the invention as the active ingredient in a plant growth regulating composition, said compounds were found to possess plant growth regulating activity when tested in accordance with the following procedure.

Soybean plants, variety Clark 63, were grown in a greenhouse or a growth chamber to the one-half expanded unifoliate stage. At that time, the plants were treated by dipping the plants into an aqueous solution of the chemical, acetone and a surfactant. After growing the plants for approximately two weeks under cool conditions (11°–14° C.), the plants were transferred to a greenhouse and grown at 24° C. Approximately four weeks after treatment, the plants were observed and compared with control plants that had been dipped into water containing only the surfactant. Table III summarizes these observations.

TABLE III

| Compound | Rate (ppm) | Observations |
| --- | --- | --- |
| 1 | 133 | Stature reduction, necrosis, stem distortion, inhibition of apical development. |
|   | 400 | Stature reduction, necrosis, stem distortion, inhibition of apical development. |
| 2 | 133 | Spindly branch growth. |
|   | 400 | Spindly branch growth. |
| 3 | 133 | Stature reduction, axillary bud development. |
|   | 400 | Stature reduction, axillary bud development, leaf inhibition. |
| 4 | 133 | No response. |
|   | 400 | No response. |
| 5 | 133 | Stature reduction, axillary bud development, inhibition of apical development. |
|   | 400 | Stature reduction, axillary bud development, leaf distortion, inhibition of apical development. |
| 6 | 266 | Stature reduction, axillary bud development, epinasty, dark foliar color, inhibition of apical development, leaf inhibition. |
| 7 | 266 | Stature reduction, leaf inhibition, epinasty, axillary bud development, dark foliar color. |
| 8 | 266 | Stem distortion, leaf inhibition, epinasty, axillary bud development, dark foliar color. |
| 9 | 266 | Stature reduction, leaf inhibition, axillary bud development, inhibition of apical devlopment. |

Compounds 2 and 3 were further tested as follows.

A number of soybean plants, variety Williams, are grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 is used as a surfactant.

When the fifth trifoliate leaf (four to five weeks) was fully expanded, the treated plants were compared with the non-treated control plants and the observations recorded.

Table IV below summarizes the results and observations made in accordance with the above procedure.

Table IV

| Compound | $\frac{kg}{h}$ | Observations |
| --- | --- | --- |
| 2 | 2.8 | Stature reduction, stem distortion, leaf distortion, leaf alteration, altered canopy, slight leaf burn. |
|   | 0.56 | Stature reduction, stem distortion, leaf distortion, leaf alteration, altered canopy, slight leaf burn. |
|   | 0.11 | Altered canopy, leaf alteration. |
| 3 | 2.8 | Stature reduction, stem distortion, leaf distortion, leaf alteration, altered canopy, slight leaf burn. |
|   | 0.56 | Stature reduction, stem distortion, leaf distortion, leaf alteration, altered canopy, slight leaf burn. |
|   | 0.11 | Leaf alteration. |

Compound 3 was further tested on the black locust tree. Seedlings of said tree were potted and placed in the greenhouse after they had been subjected to a cold temperature environment (4° C.) for a period of approximately two months. When the buds broke and new growth appeared, the trunk and foliage were treated with 50 mg of an aqueous solution of Compound 3, acetone, cyclohexanone and an emulsifier. Observations were made ranging from 7 to 57 days after treatment and comparisons with untreated control plants noted. These observations included stature reduction, leaf epinasty, stimulation of axillary buds, leaf inhibition and inhibition of branch growth.

In selecting the appropriate time and rate of application of the active ingredient, it will be recognized that precise rates will also be dependent upon the desired response, mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above. In addition, it will be recognized that single or multiple applications may be used to exert the desired response.

The above data illustrate that the compounds of the invention may be used as a herbicide or a plant growth regulant. When used as a herbicide, it is desirable that rates of application above 2.24 kilograms per hectare be utilized. When used to regulate the growth of desirable plants, rates below 5.6 kilograms per hectare, especially 0.056 to 3.36, are preferred.

In the practice of the invention, the active ingredient can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of regulating the growth of desirable plants which comprises applying to said plants an effective amount of a compound having the formula

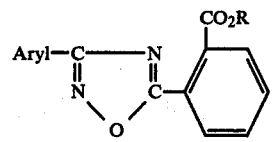

wherein R is selected from the group consisting of hydrogen, lower alkyl and agriculturally acceptable cations; aryl is phenyl substituted by one trifluoromethyl.

* * * * *